(12) United States Patent
Josse et al.

(10) Patent No.: US 9,345,583 B2
(45) Date of Patent: May 24, 2016

(54) SPINAL IMPLANT

(75) Inventors: Loic Josse, Denens (CH); Phillippe Maxy, Morbier (FR); Vincent Pointillart, Bordeaux (FR); Richard Assaker, Belgium (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 321 days.

(21) Appl. No.: 13/331,888

(22) Filed: Dec. 20, 2011

(65) Prior Publication Data

US 2013/0158665 A1    Jun. 20, 2013

(51) Int. Cl.
*A61F 2/44* (2006.01)
*A61F 2/30* (2006.01)

(52) U.S. Cl.
CPC ......... *A61F 2/4425* (2013.01); *A61F 2002/302* (2013.01); *A61F 2002/30014* (2013.01); *A61F 2002/30069* (2013.01); *A61F 2002/30504* (2013.01); *A61F 2002/30563* (2013.01); *A61F 2002/30607* (2013.01); *A61F 2002/30657* (2013.01); *A61F 2002/30822* (2013.01); *A61F 2002/30828* (2013.01); *A61F 2002/30904* (2013.01); *A61F 2310/00017* (2013.01); *A61F 2310/00023* (2013.01); *A61F 2310/00029* (2013.01)

(58) Field of Classification Search
CPC .................. A61F 2/442; A61F 2/4425; A61F 2002/30014
USPC ............................................ 623/17.11–17.16
See application file for complete search history.

(56) References Cited

U.S. PATENT DOCUMENTS

| 3,867,728 | A | 2/1975 | Stubstad et al. |
| 5,314,477 | A | 5/1994 | Marnay |
| 5,507,816 | A | 4/1996 | Bullivant |
| 5,534,030 | A | 7/1996 | Navarro et al. |
| 5,545,229 | A | 8/1996 | Parsons et al. |
| 5,676,701 | A | 10/1997 | Yuan et al. |

(Continued)

FOREIGN PATENT DOCUMENTS

| CN | 1925817 | 3/2007 |
| EP | 1041945 B1 | 5/2003 |

(Continued)

OTHER PUBLICATIONS

English translation of JP8004606.

(Continued)

*Primary Examiner* — Kevin T Truong
*Assistant Examiner* — Si Ming Ku

(57) ABSTRACT

A spinal implant including a first component, a second component and a core component is disclosed. The first component includes a first exterior surface configured for engaging a first vertebra and a first interior surface opposing the first exterior surface. The second component includes a second exterior surface configured for engaging a second vertebra and a second interior surface opposing the second exterior surface. The core component is situated between the first and second components and adhered to the first interior surface and the second interior surface, wherein at least one of the first interior surface and the second interior surface includes a concavity such that at the location of the concavity, the core component includes a corresponding convexity. Further, the core component includes a sidewall, wherein the sidewall comprises a concavity.

20 Claims, 16 Drawing Sheets

(56) References Cited

U.S. PATENT DOCUMENTS

| | | |
|---|---|---|
| 5,824,094 A | 10/1998 | Serhan et al. |
| 6,139,579 A | 10/2000 | Steffee et al. |
| 6,162,252 A | 12/2000 | Kuras et al. |
| 6,348,071 B1 | 2/2002 | Steffee et al. |
| 6,592,624 B1 | 7/2003 | Fraser et al. |
| 6,682,562 B2 | 1/2004 | Viart et al. |
| 6,706,068 B2 | 3/2004 | Ferree |
| 6,733,532 B1 | 5/2004 | Gauchet et al. |
| 7,156,848 B2 | 1/2007 | Ferree |
| 7,156,876 B2 | 1/2007 | Moumene et al. |
| 7,214,244 B2 | 5/2007 | Zubok et al. |
| 7,267,688 B2 | 9/2007 | Ferree |
| 7,452,380 B2 | 11/2008 | Zubok et al. |
| 7,857,852 B2 | 12/2010 | Kuras |
| 2003/0100951 A1 | 5/2003 | Serhan et al. |
| 2004/0030391 A1 | 2/2004 | Ferree |
| 2004/0034423 A1 | 2/2004 | Lyons et al. |
| 2004/0111155 A1 | 6/2004 | Ferree |
| 2006/0116769 A1 | 6/2006 | Marnay et al. |
| 2006/0259144 A1 * | 11/2006 | Trieu ............ 623/17.13 |
| 2007/0233262 A1 | 10/2007 | Arnin et al. |
| 2007/0270971 A1 | 11/2007 | Trieu et al. |
| 2008/0051900 A1 | 2/2008 | deVilliers et al. |
| 2008/0133011 A1 * | 6/2008 | de Villiers et al. ....... 623/17.11 |
| 2009/0076614 A1 * | 3/2009 | Arramon ............ 623/17.16 |
| 2009/0182429 A1 | 7/2009 | Humphreys et al. |
| 2009/0210059 A1 | 8/2009 | McCombe et al. |
| 2009/0210060 A1 | 8/2009 | deVilliers et al. |

FOREIGN PATENT DOCUMENTS

| | | |
|---|---|---|
| EP | 1023011 B1 | 12/2003 |
| EP | 1103237 B1 | 10/2006 |
| EP | 1405615 B1 | 10/2006 |

OTHER PUBLICATIONS

English translation of JP8004607.

* cited by examiner

SPINAL IMPLANT

FIELD OF INVENTION

The present invention is directed to spinal implants.

BACKGROUND

The present disclosure relates to spinal implants, and particularly, spinal implants for intervertebral space.

SUMMARY OF THE INVENTION

A spinal implant comprising a first component, a second component and a core component is disclosed. The first component comprises a first exterior surface configured for engaging a first vertebra and a first interior surface opposing the first exterior surface. The second component comprises a second exterior surface configured for engaging a second vertebra and a second interior surface opposing the second exterior surface. The core component is situated between the first and second components and adhered to the first interior surface and the second interior surface, wherein at least one of the first interior surface and the second interior surface comprises a concavity such that at the location of the concavity, the core component comprises a corresponding convexity. Further, the core component may further comprise a sidewall, wherein the sidewall comprises a concavity.

Additional aspects and features of the present disclosure will be apparent from the detailed description and claims as set forth below.

DETAILED DESCRIPTION

Figure 1:
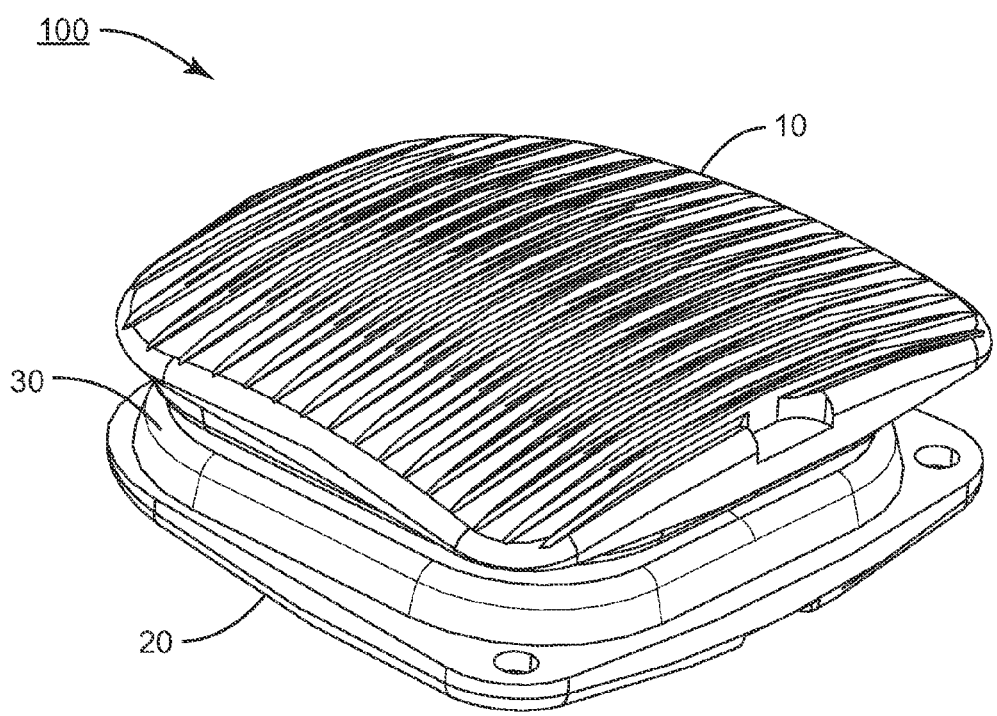
FIG. 1 is an isometric view of a spinal implant for placement in a disc space between adjacent vertebral bodies.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows an isometric view of a spinal implant 100 for placement in a disc space between adjacent vertebral bodies. The implant 100 comprises a first component 10, a second component 20 and a core component 30 situated between the first component 10 and the second component 20. As shown in FIG. 1, the core component 30 is adhered to the first component 10 and the second component 20.

Figure 1A:
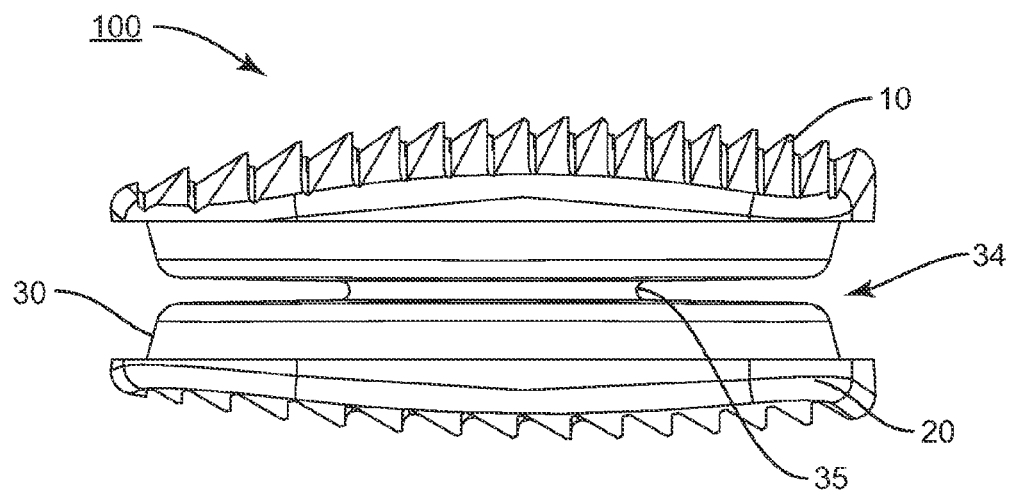
FIG. 1A is a side view of the spinal implant of FIG. 1.
Figure 1B:
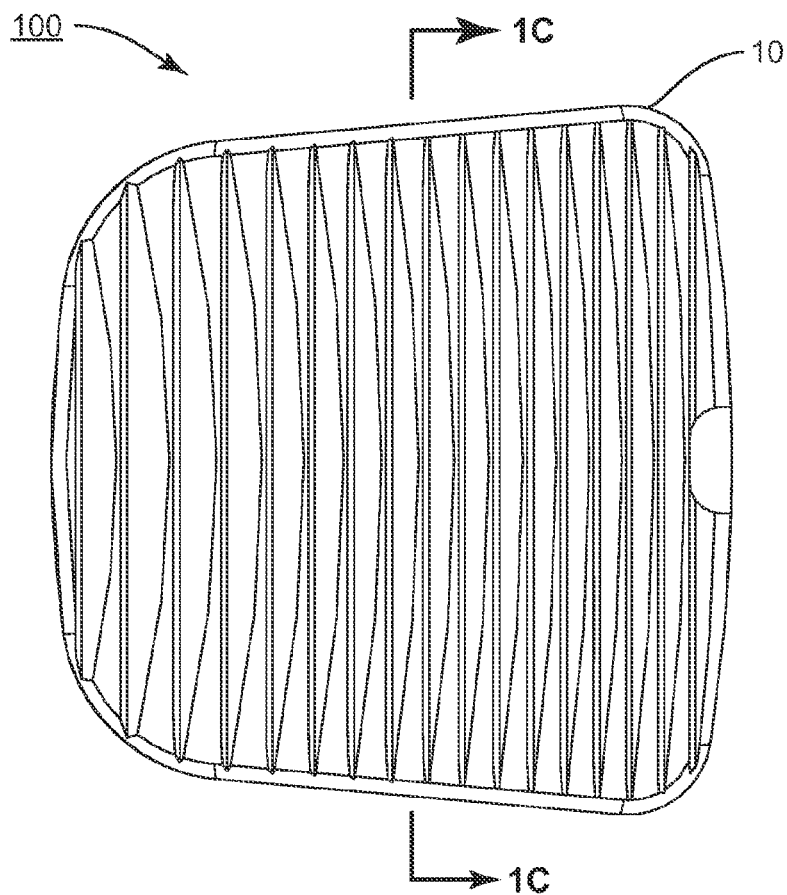
FIG. 1B is a top view of the spinal implant of FIG. 1.
Figure 1C:
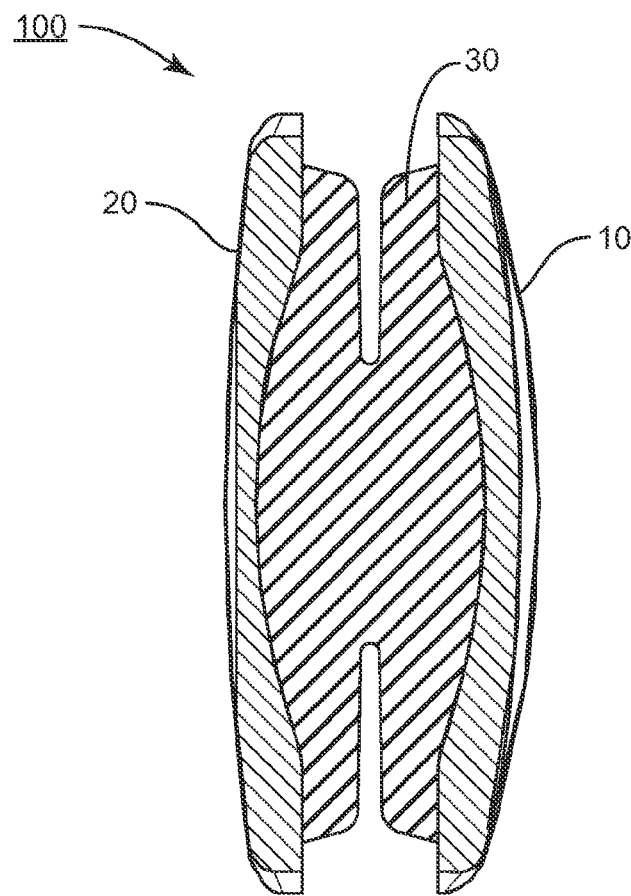
FIG. 1C is a cross-sectional side view of the spinal implant of FIG. 1 taken along line 1C-1C of FIG. 1B.
Figure 1D:
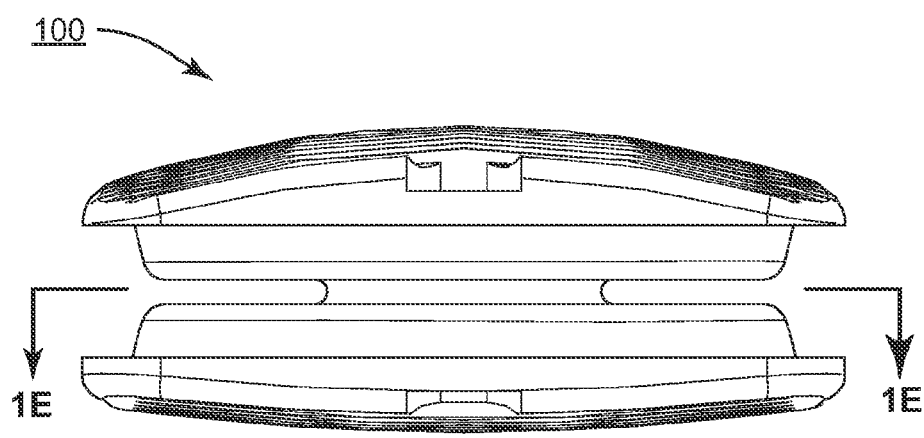
FIG. 1D is a front view of the spinal implant of FIG. 1.
Figure 1E:
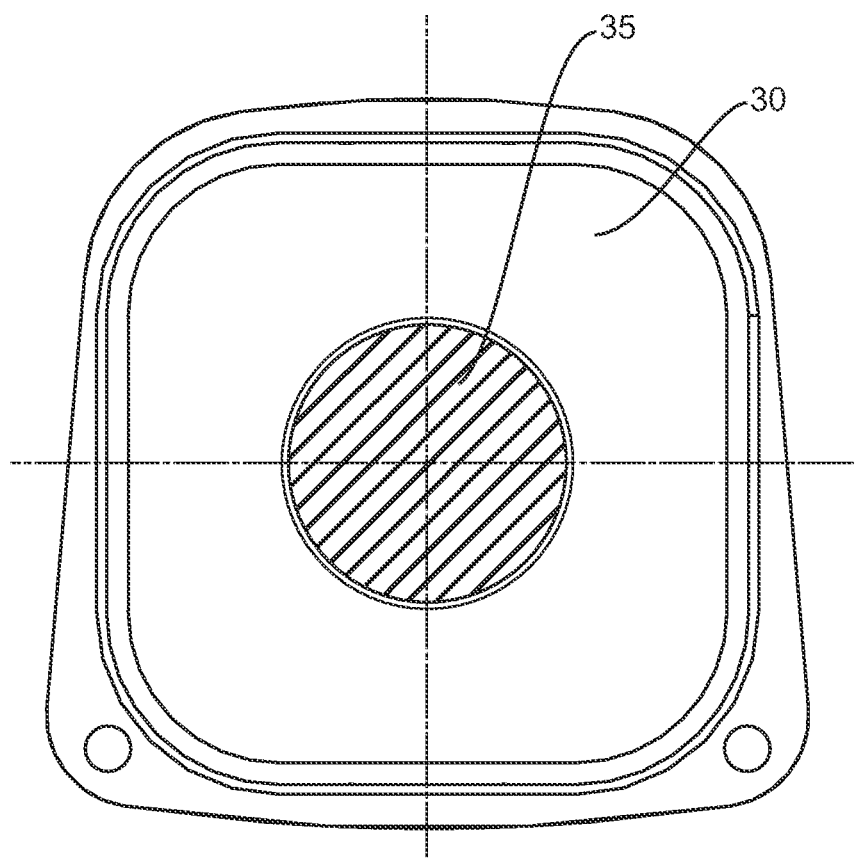
FIG. 1E is a cross-sectional top view of the spinal implant of FIG. 1 taken along line 1E-1E of FIG. 1D.

FIG. 1A shows a side view of spinal implant 100. As shown in FIG. 1A, the core component 30 comprises a concavity 34, which results in a central core component 35. FIG. 1B shows a top view of spinal implant 100. FIG. 1C shows a cross-sectional side view of spinal implant 100 taken along line 1C-1C of FIG. 1B. FIG. 1D shows a front view of spinal implant 100. FIG. 1E shows a cross-sectional top view of spinal implant 100 taken along line 1E-1E of FIG. 1D. Note that line 1E-1E is drawn through the central core component 35 of core component 30 so the central core component 35 is shown in "cross-hatching."

Figure 1F:
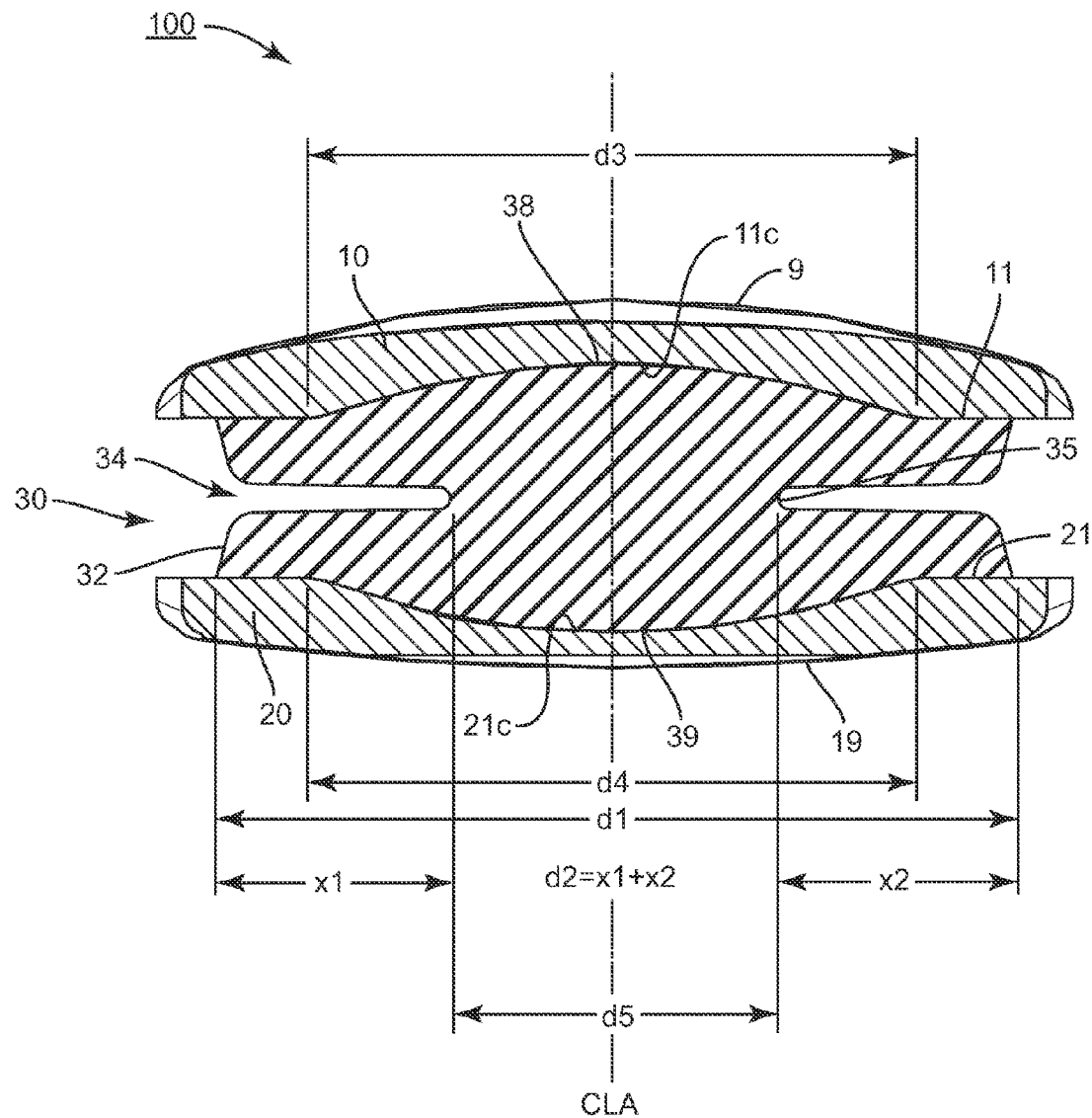
FIG. 1F is an enlarged cross-sectional side view of the spinal implant of FIG. 1 taken along line 1C-1C of FIG. 1B.

FIG. 1F shows an enlarged view of FIG. 1C, so it is an enlarged cross-sectional side view of spinal implant 100 taken along line 1C-1C of FIG. 1B. As shown in FIG. 1F, the first component 10 comprises a first exterior surface 9 configured for engaging a first vertebra, and a first interior surface 11 opposing the first exterior surface 9. The second component 20 comprises a second exterior surface 19 configured for engaging a second vertebra, and a second interior surface 21 opposing the second exterior surface 19.

As shown in FIG. 1F, the spinal implant 100 comprises a central longitudinal axis CLA situated substantially in the center of the spinal implant 100, wherein along the central longitudinal axis CLA, the components of the spinal implant 100 are situated in an order of first component 10, core component 30 and second component 20. Further, as shown in FIG. 1F, the core component 30 comprises a sidewall 32 that extends 360 degrees around the central longitudinal axis CLA. Further, the sidewall 32 comprises concavity 34, which results in the central core component 35. Further, as shown in FIG. 1F, the concavity 34 in the sidewall 32 of the core component 30 is situated at a location about the central longitudinal axis CLA that is substantially midway between the first inner surface 11 and the second inner surface 21 and substantially perpendicular to the central longitudinal axis CLA.

The term "substantially" or "substantial" as used herein may be applied to modify any quantitative representation which could permissibly vary without resulting in a change in the basic function to which it is related. For example, while concavities 11C and 21C lie in a direction substantially parallel to the central longitudinal axis CLA, it is not necessary that each concavity 11C or 21C lie in a direction exactly parallel to the central longitudinal axis CLA. Similarly, the exact center of the spinal implant 100 may be difficult to determine, especially when the spinal implant 100 is not symmetrical in all directions. Thus, the central longitudinal axis CLA need only be located substantially in the center of the spinal implant 100.

As shown in FIG. 1F, the core component 30 is situated between the first component 10 and the second component 20 and adhered to the first interior surface 11 and the second interior surface 21. Further, in spinal implant 100, at least one of the first interior surface 11 and the second interior surface 21 comprises a concavity 11C or 21C such that at the location of the concavity 11C or 21C, the core component 30 comprises a corresponding convexity 38 or 39. Specifically, as shown in FIG. 1F, the first interior surface 11 comprises a first concavity 11C such that at the location of the first concavity 11C, the core component 30 comprises a corresponding convexity 38. Similarly, as shown in FIG. 1F, the second interior surface 21 comprises a second concavity 21C such that at the location of the second concavity 21C, the core component 30 comprises a corresponding convexity 39.

Further, as shown in the embodiment of FIG. 1F, the core component 30 extends over a first distance d1 in a direction substantially perpendicular to the central longitudinal axis CLA and the concavity 34 in the sidewall of the core component extends over a second distance d2 (as shown in FIG. 1F, the second distance d2=distance x1+distance x2) in a direction substantially perpendicular to the central longitudinal axis CLA, wherein the second distance d2 is more than half of the first distance d1. Note that the shape of the sidewall 34 may vary and thus affect the length of distance d2, for example. For example, the shape of the sidewall 34 may be curvilinear or linear and/or may be substantially parallel with the central longitudinal axis CLA or may be slightly oblique, for example, as shown in FIG. 1F.

Further, as shown in the embodiment of FIG. 1F, the concavity 11C in the first inner surface 11 and the concavity 21C in the second inner surface 21 each lie about the central longitudinal axis CLA and each concavity 11C and 21C lies in a direction substantially parallel to the central longitudinal axis and spans an area that extends substantially perpendicular to the central longitudinal axis CLA along the first inner surface 11 and the second inner surface 21, respectively. Further, as shown in the embodiment of FIG. 1F, the concavity 11C in the first inner surface 11 extends over a third distance d3 about the central longitudinal axis CLA and the concavity in the second inner surface 21 extends over a fourth distance d4 about the central longitudinal axis CLA.

Further, as shown in the embodiment of FIG. 1F, at the location of the concavity 34 in the sidewall 32 of the core 30, the core component 30 (or central core component 35) extends in a direction substantially perpendicular to the central longitudinal axis CLA for a fifth distance d5, wherein each of the third and fourth distances d3 and d4 are greater than the fifth distance d5. In other embodiments, one or both of the third and fourth distances d3 and d4 may be lesser than the fifth distance d5. Any combination is contemplated. For examples, in yet other embodiments, the third distance d3 may be equal to, greater than or lesser than the fifth distance d5 and the fourth distance d4 may be equal to, greater than or lesser than the fifth distance d5.

As shown in FIG. 1F, in some embodiments of the spinal implant 100, the first component 10 and the second component 20 is rigid and the core component 30 is not rigid. In some embodiments of the spinal implant 100, the first component 10 and the second component 20 each comprise a metal material and the core component 30 comprises an elastomeric material. Depending on the desired attributes, many combinations of materials and physical properties are possible. For example, although the first and second components 10 and 20 may not be rigid, the core component 30 may be an elastomeric material.

Further, as shown in the embodiment of FIG. 1F and where the first and second components 10 and 20 comprise a rigid material and where the core component comprises an elastomeric material, the concavities 11C and 21C help reduce the shear stresses throughout the spinal implant 100 and particularly at the junction of the core component 30 and the surrounding components 10 and 20. In general, with embodiments of this type, the larger the concavity, there is a greater amount of elastomeric material and thus, the greater the amount that the elastomeric material of the core component 30 is allowed to move. Thus, with more movement of the core component 30, there is greater potential for a reduction in shear forces. More specifically, the shapes of concavities 11C and 21C make it possible to direct and concentrate the forces of vertical compression toward the center of core component 30. Consequently, concavities 11C and 21C make it possible to better absorb the shearing forces to which the implant 100 would be subjected.

Further, as shown in the embodiment of FIG. 1F and where the first and second components 10 and 20 comprise a rigid material and where the core component comprises an elastomeric material, concavity 34 helps reduce the forces between the core component 30 and the first and second components 10 and 20, forces that otherwise may lead to separation of the core component 30 from one or both components 10 and 20. With such embodiments where there is a feature such as concavity 34, the concavities 11C and 21C and corresponding convexities 38 and 39 further reduce the shear stresses throughout the spinal implant 100 and particularly at the junction of the core component 30 to the surrounding components 10 and 20. Further, concavity 34 reinforces the non-linear character of the deformation of the implant 100 under loading and then provides the spinal implant 100 with an ability to imitate the nonlinear behavior of a natural anatomical intervertebral disc. As shown in FIG. 1F, concavity 34 is substantially symmetrical and perpendicular to central longitudinal axis CLA.

Figure 1G:
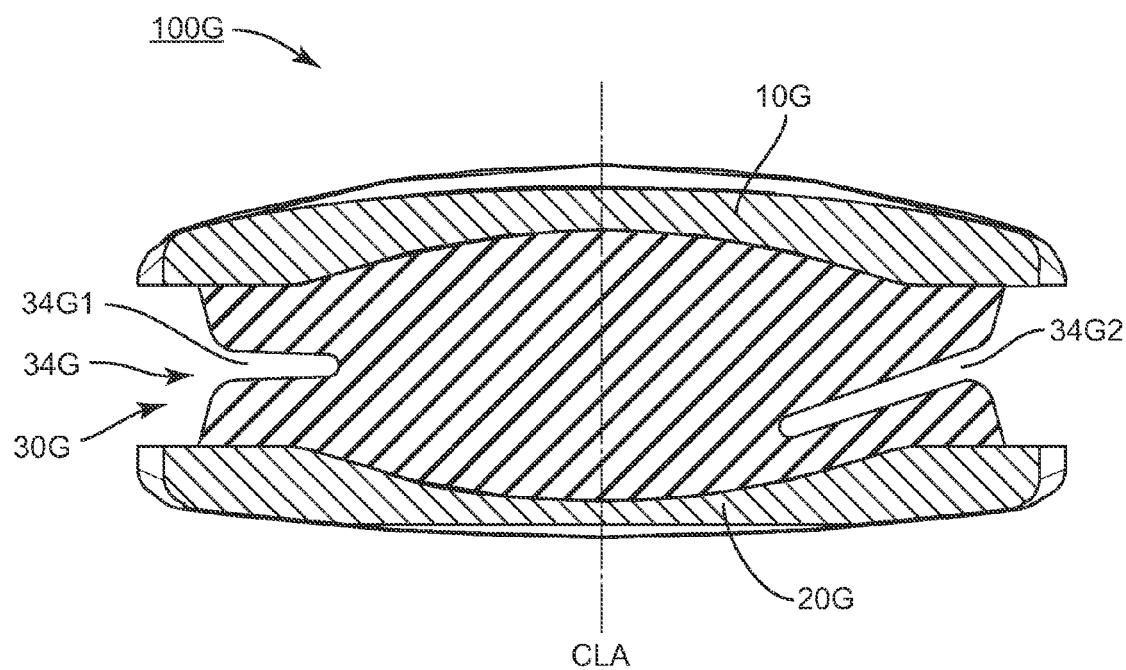
FIG. 1G is an enlarged cross-sectional side view of a spinal implant taken along a mid-line.

Note that it is not necessary, however, that a concavity (such as, for example concavity 34 of implant 100) lie in a direction substantially perpendicular to the central longitudinal axis CLA. Similarly, it is not necessary for a concavity to be symmetric about the central longitudinal axis CLA. For example, when a concavity is asymmetrical, motions of the spinal implant (for example, an amplitude and load-displacement curve) will be different from one side to the other one. For example, FIG. 1G shows an enlarged cross-sectional side view of spinal implant 100G taken along a mid-line, similar to FIG. 1F. As shown in FIG. 1G, spinal implant 100G comprises a first component 10G, a second component 20G and a core component 30G situated between the first component 10G and the second component 20G. Further, as shown in FIG. 1G, core component 34 comprises a concavity 34G that is not symmetrical about central longitudinal axis CLA. More specifically, as shown in the cross-sectional side view of the implant 100G of FIG. 1G, one lateral side of the core component 34 has a concavity 34G1 that lies in a direction substantially perpendicular to the central longitudinal axis CLA, while another lateral side of the core component 34 has a concavity 34G1 that lies in a direction that is not substantially perpendicular to the central longitudinal axis CLA, but lies in a direction that is relatively oblique to the central longitudinal axis CLA. As another example, a central core component such as central core component 35 (created by concavity 34) may be oblong or elliptical in cross-sectional shape, i.e., instead of circular in cross-sectional shape—as shown in FIG. 1E, for example. Such a central core component would not be substantially symmetrical about the central longitudinal axis CLA, but central core component 35 would be considered symmetrical about the central longitudinal axis CLA.

Figure 2:
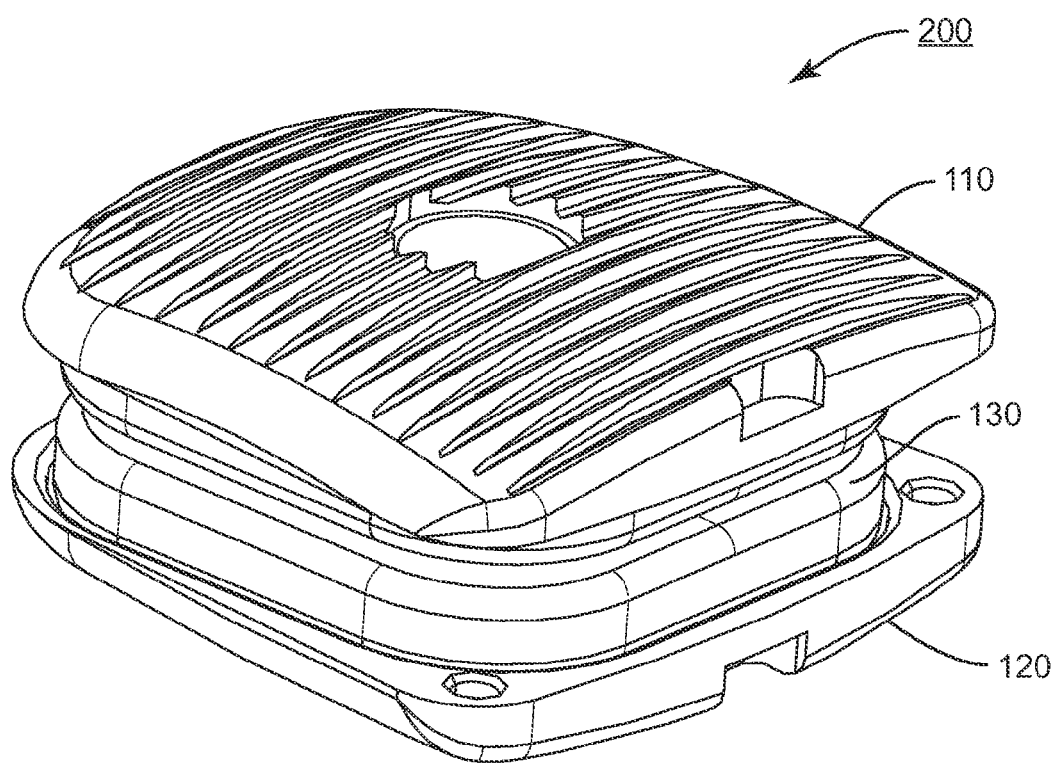
FIG. 2 is an isometric view of a spinal implant for placement in a disc space between adjacent vertebral bodies.

FIG. 2 shows an isometric view of a spinal implant 200 for placement in a disc space between adjacent vertebral bodies. The implant 200 comprises a first component 110, a second component 120 and a core component 130 situated between the first component 110 and the second component 120. As shown in FIG. 2, the core component 130 is adhered to the first component 110 and the second component 120.

Figure 2A:
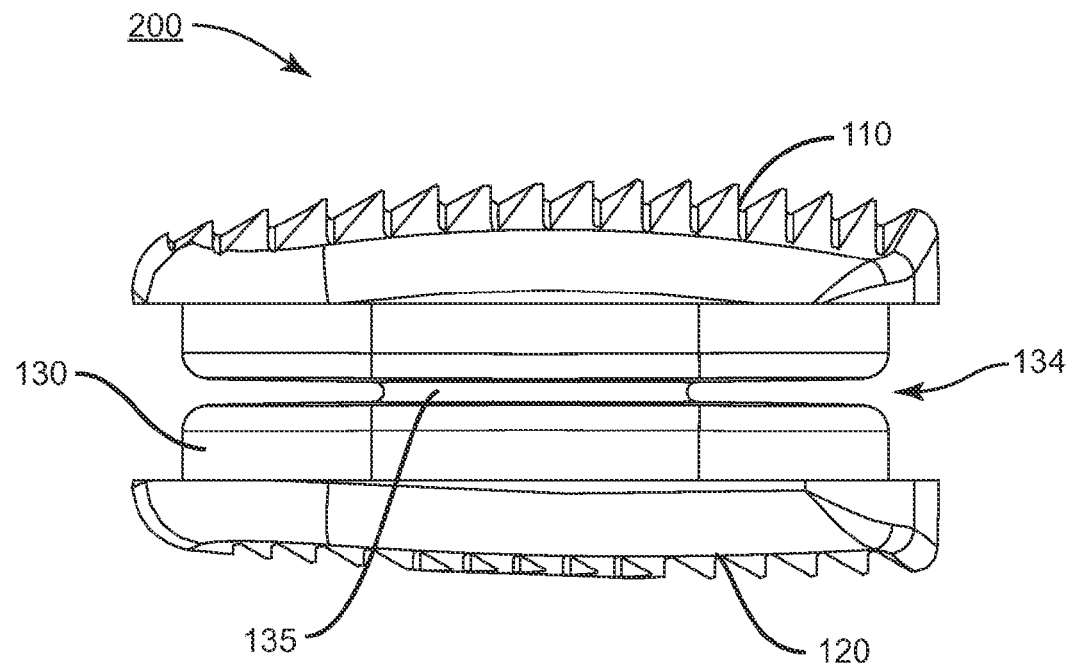
FIG. 2A is a side view of the spinal implant of FIG. 2.
Figure 2B:
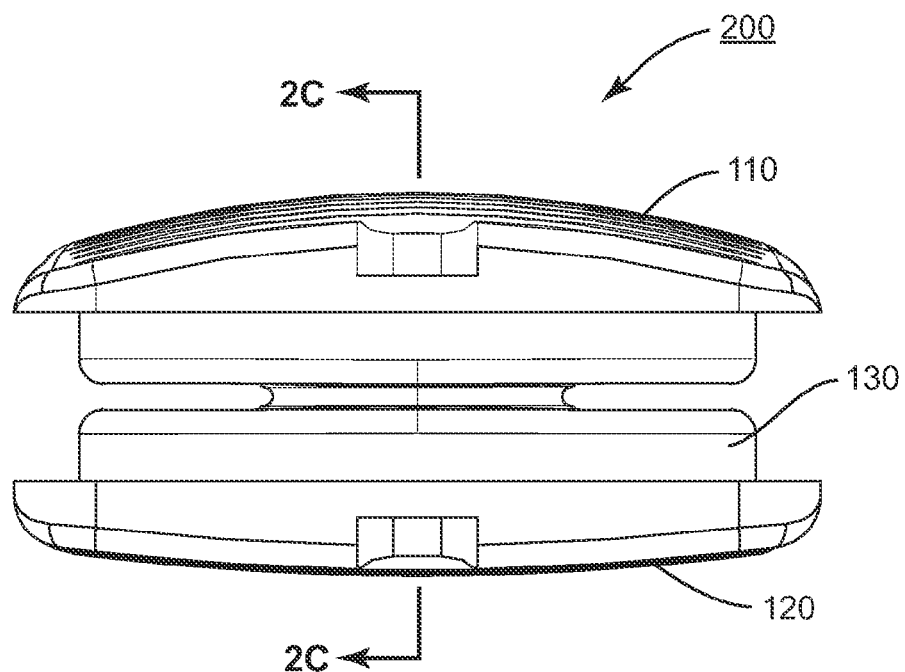
FIG. 2B is a front view of the spinal implant of FIG. 2.
Figure 2C:
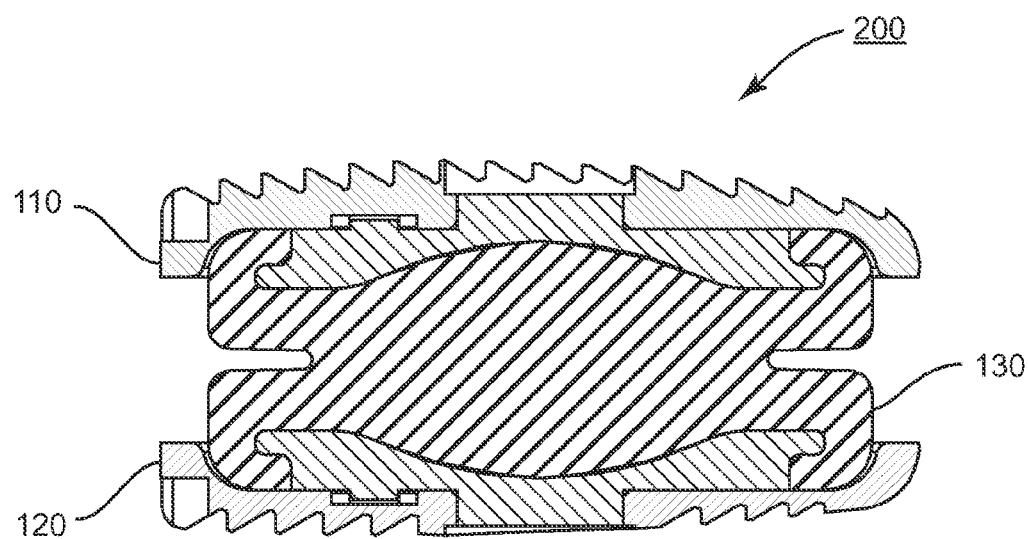
FIG. 2C is a cross-sectional side view of the spinal implant of FIG. 2 taken along line 2C-2C of FIG. 2B.
Figure 2D:
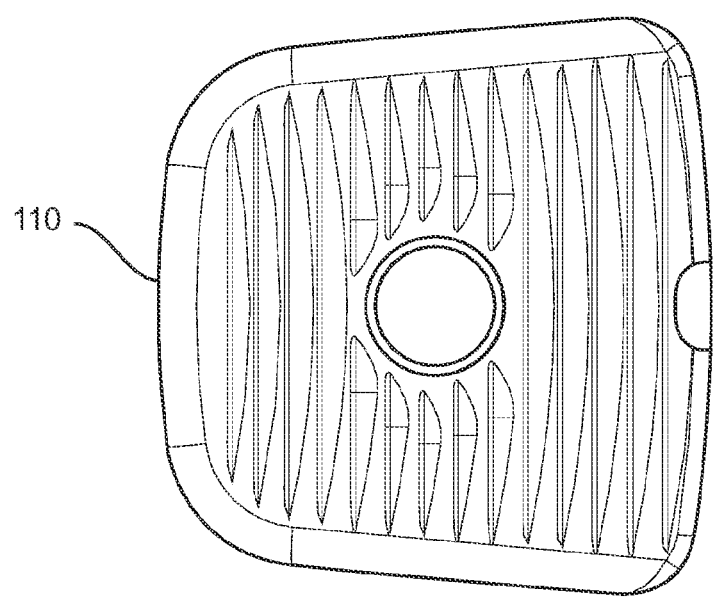
FIG. 2D is a top view of the spinal implant of FIG. 2.

FIG. 2A shows a side view of spinal implant 200. As shown in FIG. 2A, the core component 130 comprises a concavity 134, which results in a central core component 135. FIG. 2B shows a front view of spinal implant 200. FIG. 2C shows a cross-sectional side view of spinal implant 200 taken along line 2C-2C of FIG. 2B. FIG. 2D shows a top view of spinal implant 200.

Figure 2E:
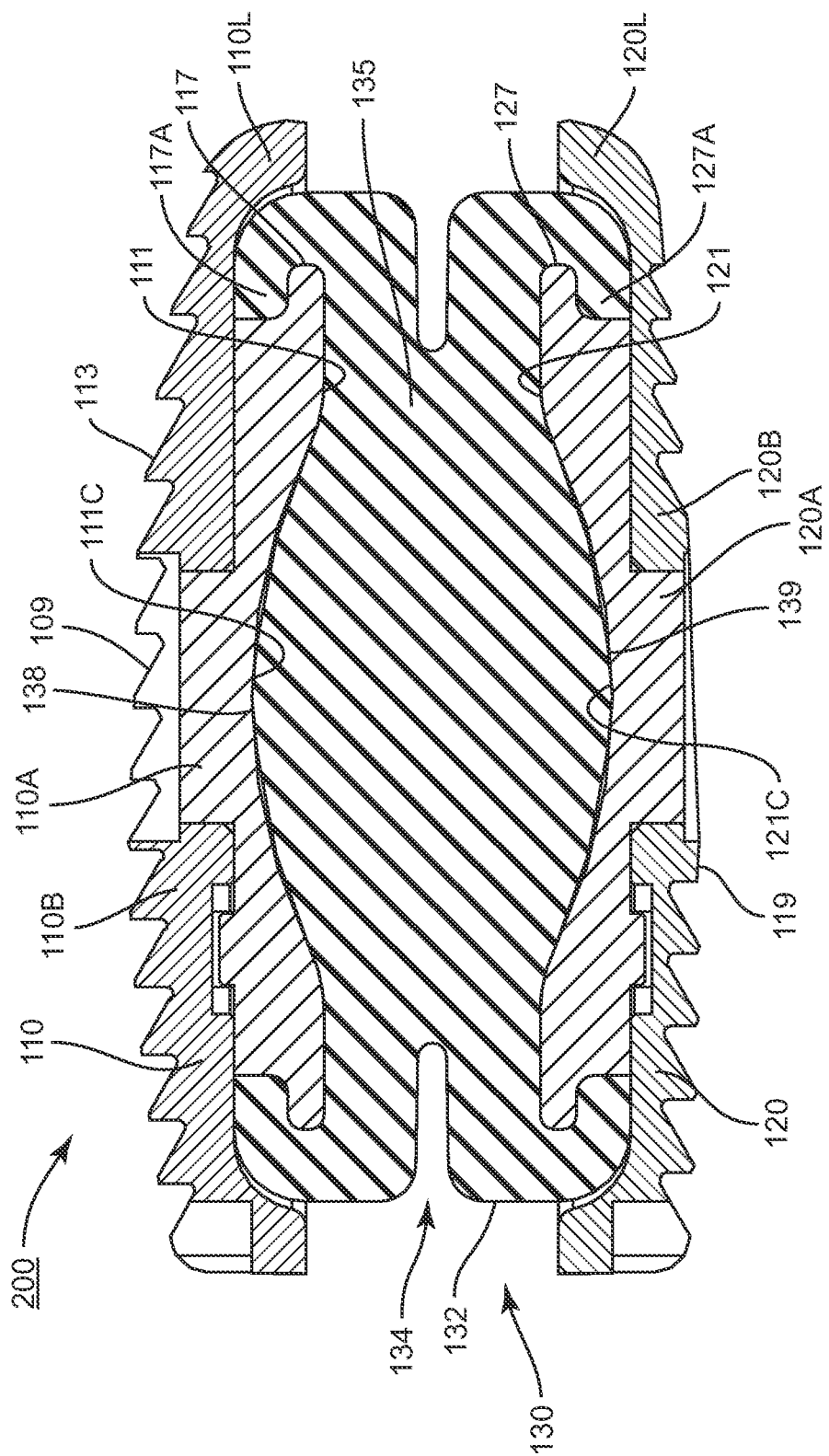
FIG. 2E is an enlarged cross-sectional side view of the spinal implant of FIG. 2 taken along line 2C-2C of FIG. 2B.

FIG. 2E shows an enlarged view of FIG. 2C, so it is an enlarged cross-sectional side view of spinal implant 200 taken along line 2C-2C of FIG. 2B. As shown in FIG. 2E, the first component 110 comprises a first exterior surface 109 configured for engaging a first vertebra, and a first interior surface 111 opposing the first exterior surface 109. The second component 120 comprises a second exterior surface 119 configured for engaging a second vertebra, and a second interior surface 121 opposing the second exterior surface 119.

As shown in FIG. 2E, the core component 130 comprises a sidewall 132 that extends 360 degrees around the central longitudinal axis of spinal implant 130. With respect to spinal implant 200 as well as all other spinal implants described herein, and even if their reference markers are not shown in the figures, note that the central longitudinal axis CLA, and distances d1, d2, d3, d4 and d5 are all situated in similar locations and measured in the same manner as described above with respect to spinal implant 100 of FIG. 1F. Further, as shown in FIG. 2E, the sidewall 132 comprises concavity 134, which results in the central core component 135. Further, as shown in FIG. 2E, the concavity 134 in the sidewall 132 of the core component 130 is situated at a location about the central longitudinal axis that is substantially midway between the first inner surface 111 and the second inner surface 121 and substantially perpendicular to the central longitudinal axis.

As shown in FIG. 2E, the core component 130 is situated between the first component 110 and the second component 120 and adhered to the first interior surface 111 and the second interior surface 121. Further, with respect to spinal implant 200, at least one of the first interior surface 111 and the second interior surface 121 comprises a concavity 111C or 121C such that at the location of the concavity 111C or 121C, the core component 130 comprises a corresponding convexity 138 or 139. Specifically, as shown in FIG. 2E, the first interior surface 111 comprises a first concavity 111C such that at the location of the first concavity 111C, the core component 130 comprises a corresponding convexity 138. Similarly, as shown in FIG. 2E, the second interior surface 121 comprises a second concavity 121C such that at the location of the second concavity 121C, the core component 130 comprises a corresponding convexity 139.

Further, as shown in the embodiment of FIG. 2E, the core component 130 extends over a first distance d1 in a direction substantially perpendicular to the central longitudinal axis and the concavity 134 in the sidewall of the core component extends over a second distance d2 in a direction substantially perpendicular to the central longitudinal axis, wherein the second distance d2 is less than half of the first distance d1. This relationship may vary and, for example, may be such that the second distance d2 is more than half of the first distance d1.

Further, as shown in the embodiment of FIG. 2E, the concavity 111C in the first inner surface 111 and the concavity 121C in the second inner surface 121 each lie about the central longitudinal axis and each concavity 111C and 121C lies in a direction substantially parallel to the central longitudinal axis and spans an area that extends substantially perpendicular to the central longitudinal axis along the first inner surface 111 and the second inner surface 121, respectively. Further, as shown in the embodiment of FIG. 2E, the concavity 111C in the first inner surface 111 extends over a third distance d3 about the central longitudinal axis and the concavity in the second inner surface 121 extends over a fourth distance d4 about the central longitudinal axis. As shown in FIG. 2E, the third and fourth distances d3 and d4 extend almost the entire length of the first and second inner surfaces 111 and 121, respectively.

Further, as shown in the embodiment of FIG. 2E, at the location of the concavity 134 in the sidewall 132 of the core 130, the core component 130 (or central core component 135) extends in a direction substantially perpendicular to the central longitudinal axis for a fifth distance d5, wherein each of the third and fourth distances d3 and d4 are shorter than the fifth distance d5. This relationship may vary and, for example, may be such that each of the distances d3 and d4 are greater than the fifth distance d5. In other embodiments, one or both of the third and fourth distances d3 and d4 may be lesser than the fifth distance d5. Any combination is contemplated. For examples, in yet other embodiments, the third distance d3 may be equal to, greater than or lesser than the fifth distance d5 and the fourth distance d4 may be equal to, greater than or lesser than the fifth distance d5.

As with the embodiment of spinal implant 100 shown in FIG. 1F, the embodiment of spinal implant 200 shown in FIG. 2E may have a variety of material combinations, all selected to meet certain design criteria. In addition to the differences already addressed, however, there are some differences between spinal implant 200 and spinal implant 100. For example, with respect to spinal implant 200, the first component 110 has a first flange 117 and the second component 120 has a second flange 127. Further, the core component 130 has a first core flange 117A that corresponds to and engages the first flange 117, and a second core flange 127A that corresponds to and engages the second flange 127. Note that, in the embodiment shown in FIG. 2E, the central core component 135 is adhered to the first and second components 110 and 120, but the first flange 117A and the second flange 127A may be in contact with but not adhered to respective first and second components 110 and 120. In other embodiments, for example, those described below having flanges similar to flanges 117A and 127A, the flanges may or may not be adhered to their respective first and second components.

Another difference between spinal implant 200 and spinal implant 100 is that each outer surface 109 and 119 has a plurality of bone-engaging teeth or fins 113. As also shown in FIGS. 2 and 2D, the fins 113 extend laterally across the top and bottom outer surfaces 109 and 119. These fins 113 may help with integration of the spinal implant 200 on the bony surfaces of vertebral bodies between which the spinal implant 200 is intended to reside.

Another difference between spinal implant 200 and spinal implant 100 is that the first and second components 110 and 120 of spinal implant 200 comprise two parts. Specifically, as shown in FIG. 2E, the first component 110 comprises an inner portion 110A and an outer portion 110B, whereas the second component 120 comprises an inner portion 120A and an outer portion 120B. Further, as shown in FIG. 2E, the outer portions 110B and 120B each further comprise a lip 110L and 120L, respectively, that each are directed inward toward the other component.

Figure 3:
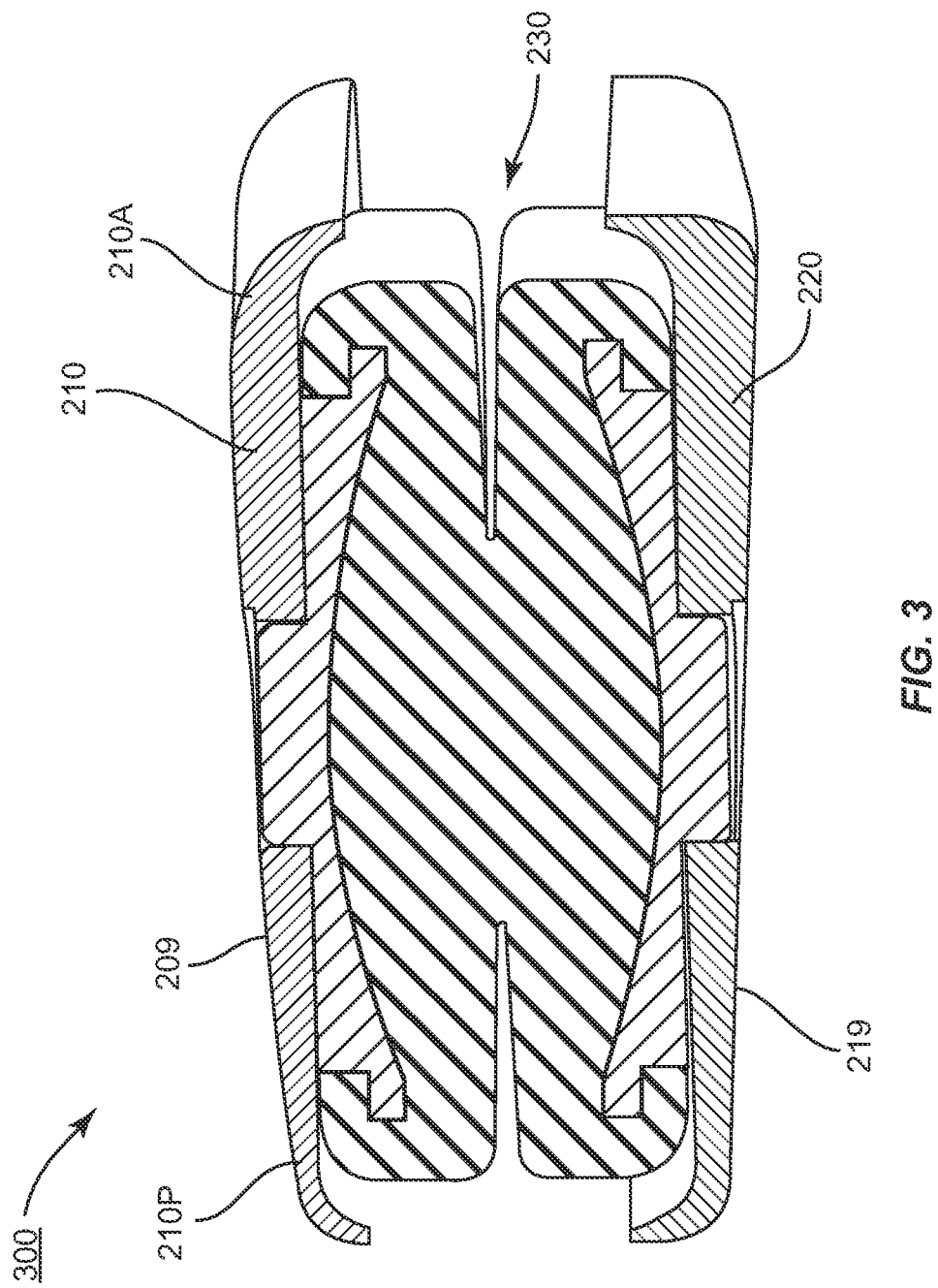
FIG. 3 is a cross-sectional side view of a spinal implant at a mid-line of the implant.

As FIGS. 1F and 2E show cross-sectional side views of spinal implants 100 and 200, respectively, FIG. 3 shows a cross-sectional side view of a spinal implant 300 at a mid-line of the implant 300. The implant 300 comprises a first component 210, a second component 220 and a core component 230 situated between the first component 210 and the second component 220. As shown in FIG. 3, the core component 230, or more specifically, its central core component is adhered to the first component 210 and the second component 220, but the flange portions may not be adhered to the first and second components 210 and 220. As shown in FIG. 3, the spinal implant 300 is similar to spinal implant 200, but the outer surfaces 209 and 219 of implant 300 do not have any fins (as shown in FIG. 2E as fins 113). Note that FIG. 3 shows that an implant such as implant 300 may have "built-in" lordosis or an angle already built in to the implant to accommodate for a natural curvature of the spine. For example, FIG. 3 shows first component 210 comprised of an anterior portion 210A and a posterior portion 210P, wherein anterior portion 210A is thicker (in vertical height, i.e., in a direction substantially parallel to the central longitudinal axis of the implant) than the posterior portion 210P. This "built-in" lordosis feature may be present in the first component 210, the second component 220 or both components 210 and 220.

Figure 4:
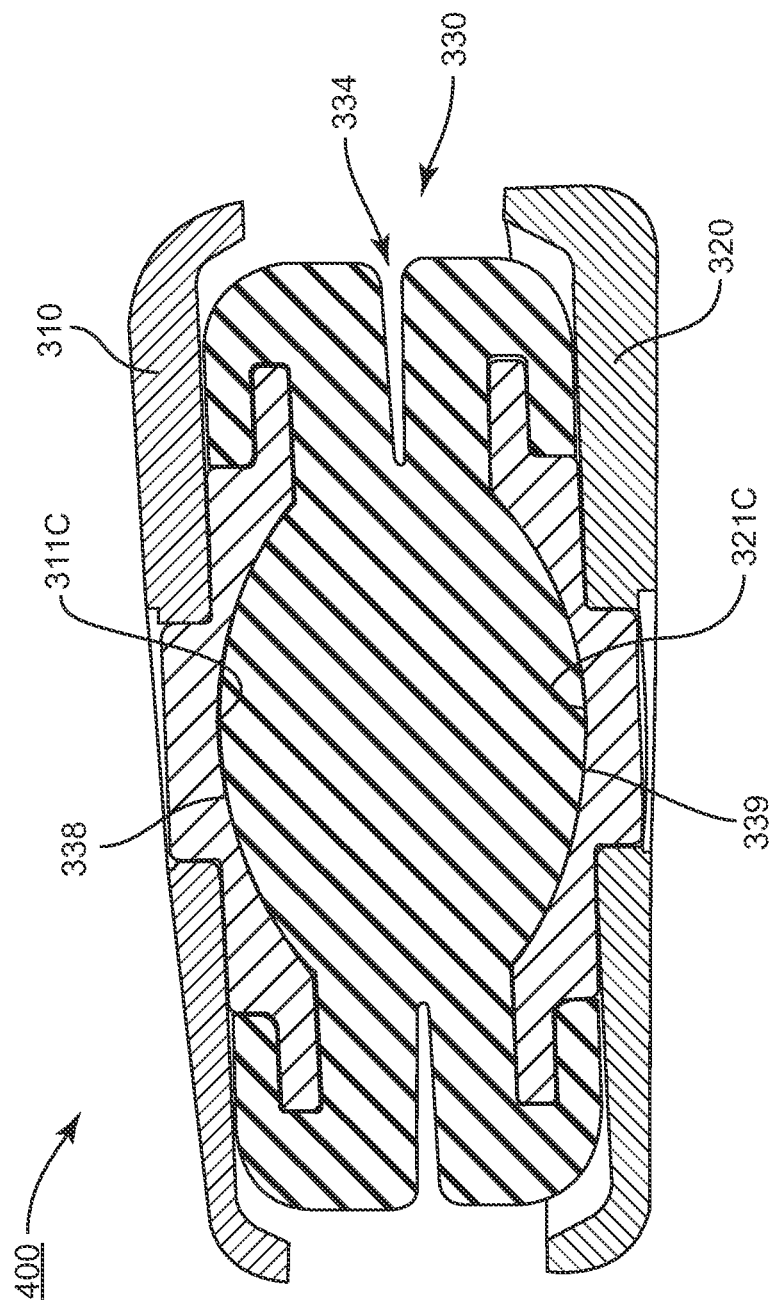
FIG. 4 is a cross-sectional side view of a spinal implant at a mid-line of the implant.

FIG. 4 shows a cross-sectional side view of a spinal implant 400 at a mid-line of the implant 400. The implant 400 comprises a first component 310, a second component 320 and a core component 330 situated between the first component 310 and the second component 320. As shown in FIG. 4, the core component 330, or more specifically, its central core component is adhered to the first component 310 and the second component 320, but the flange portions may not be adhered to the first and second components 310 and 320. As shown in FIG. 4, the spinal implant 400 is similar to spinal implant 300, but the concavities 311C and 321C each have a different shape. Specifically, as shown in FIG. 4, each of concavities 311C and 321C extend a proportionally greater amount in the vertical direction (i.e., a direction substantially parallel to the central longitudinal axis of the implant), but extend proportionally less in the horizontal direction (i.e., a direction substantially perpendicular to the central longitudinal axis of the implant). In particular, distance d5 is greater than distance d2, and distances d3 and d4 are each less than distance d5.

Figure 5:
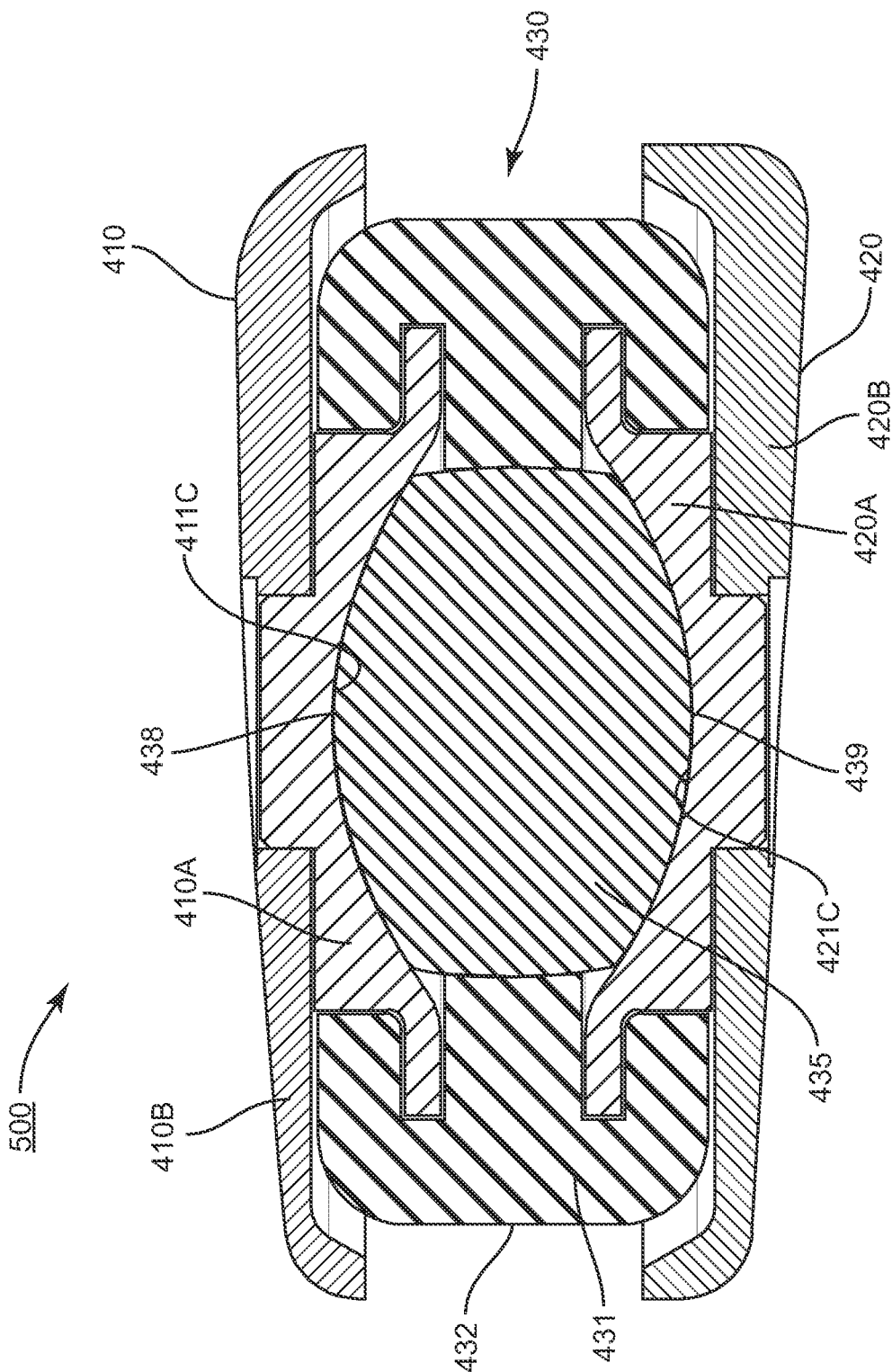
FIG. 5 is a cross-sectional side view of a spinal implant at a mid-line of the implant.

FIG. 5 shows a cross-sectional side view of a spinal implant 500 at a mid-line of the implant 500. The implant 500 comprises a first component 410, a second component 420 and a core component 430 situated between the first component 410 and the second component 420. Also, as shown in FIG. 5, the core component 430 of spinal implant 500 comprises two distinct portions, namely a central core component 435 and an outer core component 431. As shown in FIG. 5, the core component 430, or more specifically, its central core component 435 is adhered to the first component 410 and the second component 420. The central core component 435 comprises convexities 438 and 439 corresponding to concavities 411C and 421C in the first and second components 410 and 420, respectively. As shown in FIG. 5, the central core component 435 and an outer core component 431 may have the same or different material characteristics. For example, as shown in FIG. 5, central core component 435 may be harder than the outer core component 431. Note that when the central core component (for example 435) and the outer core component (for example 431) have different material properties, they still may be united as one core (for example 430) during the manufacturing or fabrication process. Further, note that, as shown in FIG. 5, the central core component 435 adheres to the inner portions 410A and 420A of the first and second components 410 and 420, respectively, whereas the outer core component 431 engages both the inner portions 410A and 420A and the outer portions 410B and 420B of the first and second components 410 and 420, respectively.

Figure 6:
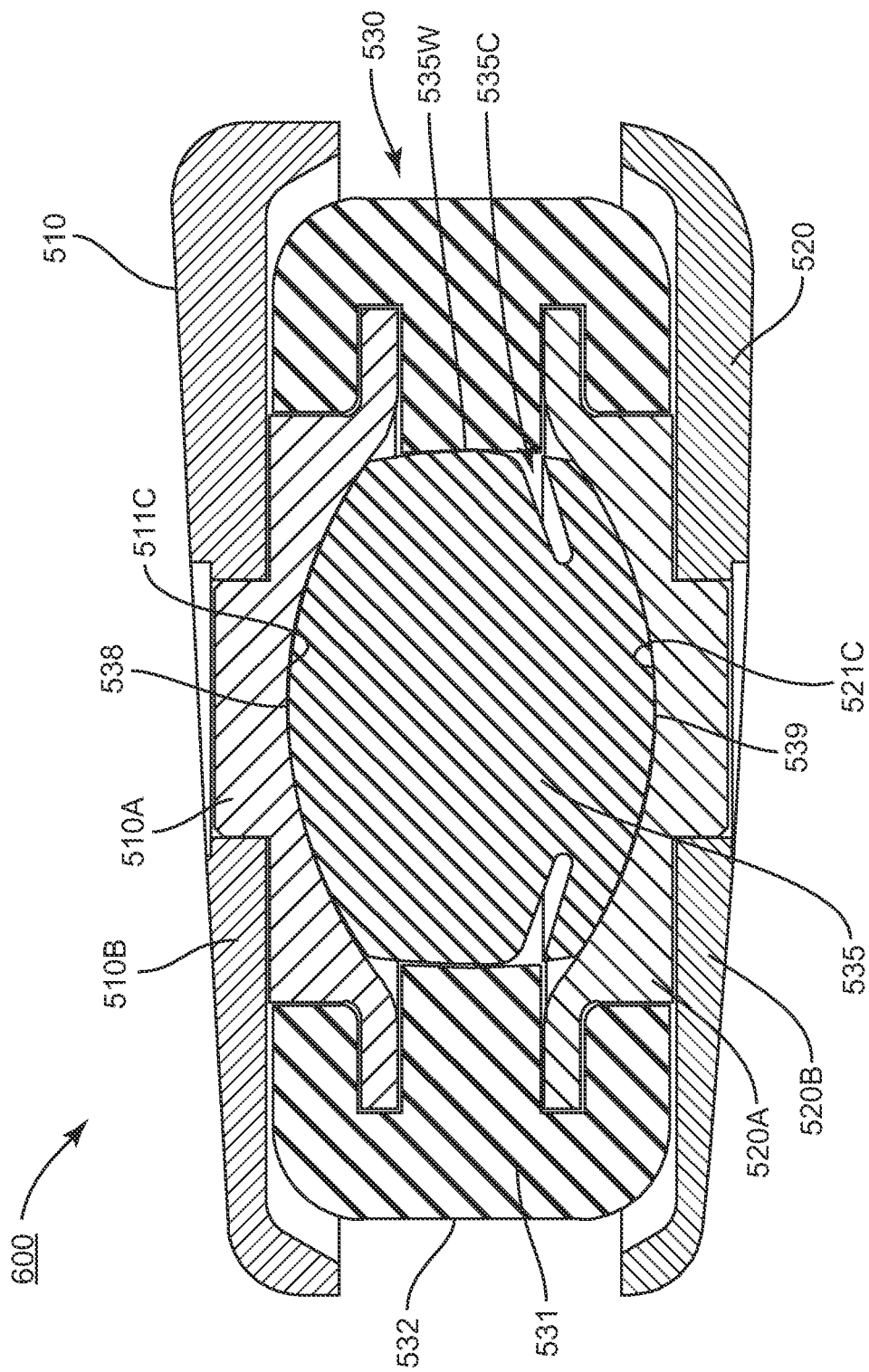
FIG. 6 is a cross-sectional side view of a spinal implant at a mid-line of the implant.

FIG. 6 shows a cross-sectional side view of a spinal implant 600 at a mid-line of the implant 600. The implant 600 comprises a first component 510, a second component 520 and a core component 530 situated between the first component 510 and the second component 520. Also, as shown in FIG. 6, the core component 530 of spinal implant 600 comprises two distinct portions, namely a central core component 535 and an outer core component 531. As shown in FIG. 6, the core component 530, or more specifically, its central core component 535 is adhered to the first component 210 and the second component 220. The central core component 535 comprises convexities 538 and 539 corresponding to concavities 511C and 521C in the first and second components 510 and 520, respectively. As shown in FIG. 6, the central core component 535 and an outer core component 531 may have the same or different material characteristics. For example, as shown in FIG. 5, central core component 435 may be harder than the outer core component 431. Further, note that, as shown in FIG. 5, the central core component 535 adheres to the inner portions 510A and 520A of the first and second components 510 and 520, respectively, whereas the outer core component 531 engages both the inner portions 510A and 520A and the outer portions 510B and 520B of the first and second components 510 and 520, respectively.

A difference between implant 600 and implant 500, however, is that the central core 535 of spinal implant 600 comprises a sidewall 535W and sidewall 535W comprises a concavity 535C. As shown in FIG. 6, concavity 535C is situated in the bottom half (vertically) of the central core component 535. Note that concavity 535C may have a shape, proportional relationship and situational relationship to central core component 535 as any of the previously-described concavities and core components. For example, concavity 535C may be larger or smaller than that shown in FIG. 6. Similarly, for example, concavity 535C may be situated midway, vertically, along the sidewall 535W of the central core component 535.

Figure 7:
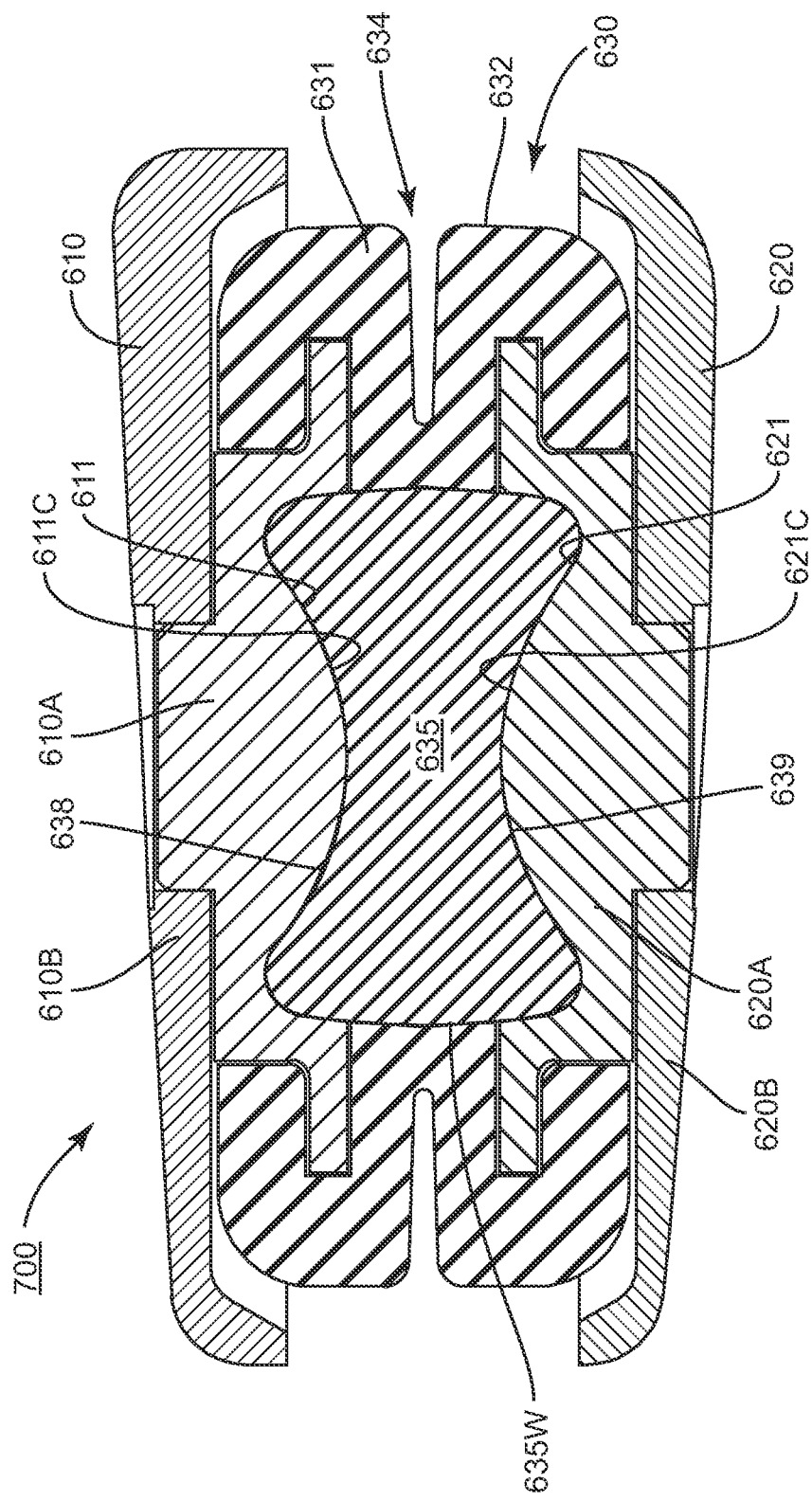
FIG. 7 is a cross-sectional side view of a spinal implant at a mid-line of the implant.

FIG. 7 shows a cross-sectional side view of a spinal implant 700 at a mid-line of the implant 700. The implant 700 comprises a first component 610, a second component 620 and a core component 630 situated between the first component 610 and the second component 620. Also, as shown in FIG. 7, the core component 630 of spinal implant 700 comprises two distinct portions, namely a central core component 635 and an outer core component 631. As shown in FIG. 7, the core component 630, or more specifically, its central core component 535 is adhered to the first component 210 and the second component 220. The central core component 635 comprises concavities 638 and 639 corresponding to the convexities 611C and 621C in the first and second components 610 and 620, respectively. As shown in FIG. 7, the central core component 635 and an outer core component 631 may have the same or different material characteristics. For example, as shown in FIG. 7, central core component 635 may be harder than the outer core component 631. Note that as opposed to the previously-described implants, spinal implant 700 is an implant in which the first interior surface 611 and the second interior surface 621 each comprise a convexity 611C and 621C, respectively, such that at the location of each convexity 611C and 621C, the core component 630—or as shown in FIG. 7, more specifically, the central core component 635—comprises a corresponding concavity 638 and 639, respectively. In addition, as shown in FIG. 7, the central core component 635 adheres to the inner portions 610A and 620A of the first and second components 610 and 620, respectively, whereas the outer core component 631 engages both the inner portions 610A and 620A and the outer portions 610B and 620B of the first and second components 610 and 620, respectively.

Further, as shown in FIG. 7, note that the core component 630 has a concavity 634 in sidewall 632. Also, as with previously-described spinal implants, note that the concavities 638 and 639 corresponding to convexities 611C and 621C in the first and second components 610 and 620 may vary in size, shape, number and location. Also, even though the core component 630, or more specifically, the central core component 635 has concavities 638 and 639 instead of convexities, this geometry still helps reduce shear forces in the implant 700 and particularly at the location of the junction between the core components 630 and the first and second components 610 and 620. More specifically, the shapes of concavities 638 and 639 make it possible to direct and concentrate the forces of vertical compression toward the center of core component 630. Consequently, concavities 638 and 639 make it possible to better absorb the shearing forces to which the implant 700 would be subjected. As noted above, however, with more elastomeric material, the greater the amount that the elastomeric material of the core component 630 is allowed to move. Thus, the result is a greater potential for a reduction in shear forces. Therefore, in general, if the core component 630 has concavities 638 and 639 instead of convexities, there is less potential for reduction of shear forces than if convexities were present.

Figure 8:
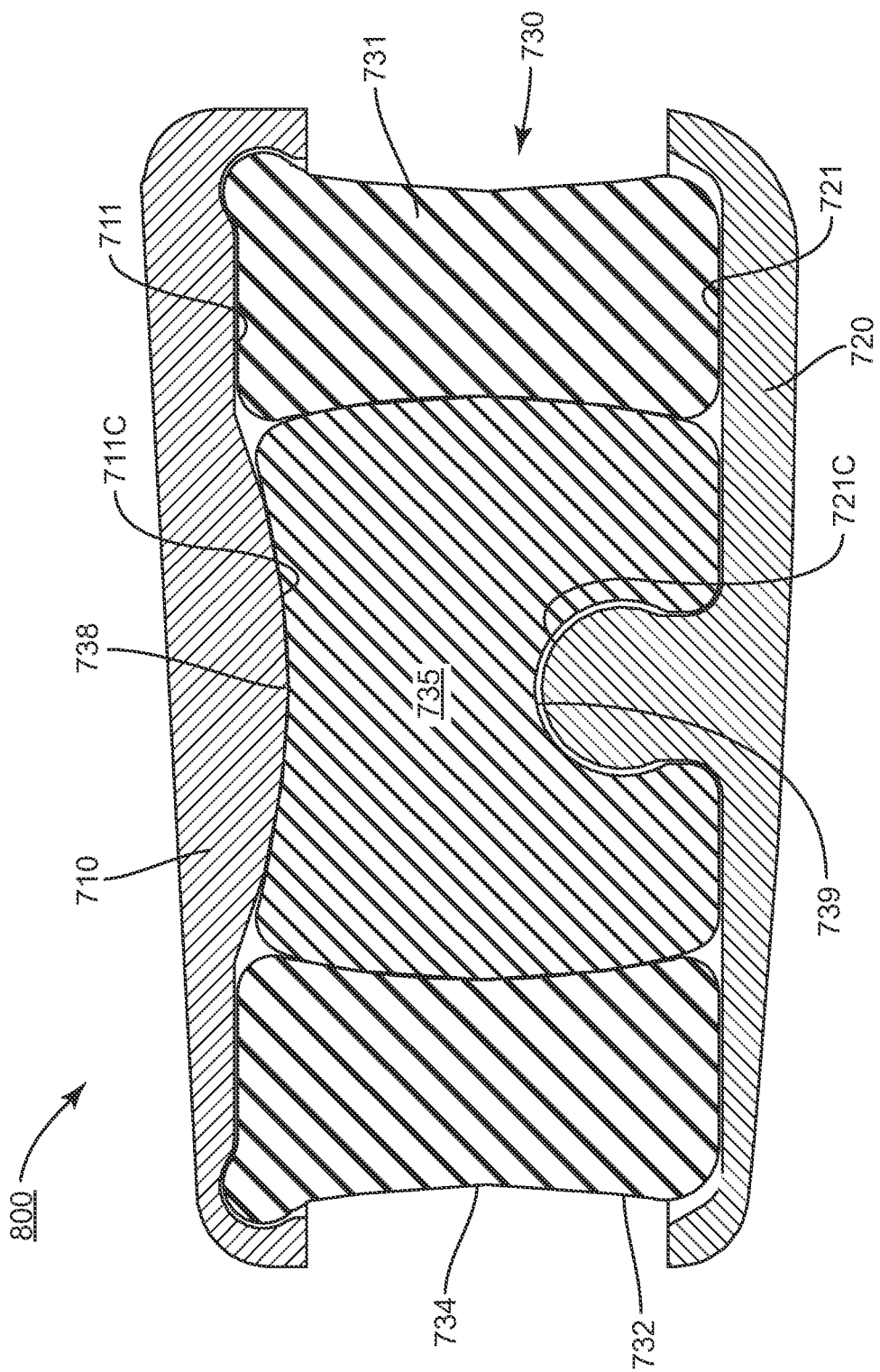
FIG. 8 is a cross-sectional side view of a spinal implant at a mid-line of the implant.

FIG. 8 shows a cross-sectional side view of a spinal implant 800 at a mid-line of the implant 800. The implant 800 comprises a first component 710, a second component 720 and a core component 730 situated between the first component 710 and the second component 720. Also, as shown in FIG. 8, the core component 730 of spinal implant 800 comprises two distinct portions, namely a central core component 735 and an outer core component 731. The central core component 735 comprises concavities 738 and 739 corresponding to convexities 711C and 721C in the first and second components 710 and 720, respectively. As shown in FIG. 8, the central core component 735 and an outer core component 731 may have the same or different material characteristics. For example, as shown in FIG. 8, central core component 735 may be harder than the outer core component 731. Note that as with spinal implant 700, implant 800 is an implant in which the first interior surface 711 and the second interior surface 721 each comprise a convexity 711C and 721C, respectively, such that at the location of each convexity 711C and 721C, the core component 730—or as shown in FIG. 8, more specifically, the central core component 735—comprises a corresponding concavity 738 and 739, respectively. In addition, as shown in FIG. 8, the central core component 735 engages the first interior surface 711 and the second interior surface 721, whereas the outer core component 731 engages the first interior surface 711 and the second interior surface 721.

Note that, as shown in FIG. 8, there is a gap shown between concavity 739 and convexity 721C and there may be other gaps between the surfaces of the core 730 and the first and second components 710 and 720. Upon loading, however, all of the surfaces between the core 730 and the first and second components 710 and 720 will be in contact and any gaps will be reduced and/or removed. Further, in the embodiment shown in FIG. 8, the core components 731 and 735 are not adhered to the first and second components 710 and 720. Note that in other embodiments, for example, implants 500, 600 and 700 described herein, while outer core components 431, 531 and 631 are shown as not adhered to their respective first and second components, they may be adhered to their respective first and second components. Similarly, as with implant 200, in other embodiments, it is possible that only the flange sections may be not adhered to the first and second components, while the remaining portions core components may be adhered to the first and second components.

Further, as shown in FIG. 8, note that the outer core component 731 has a concavity 734 in sidewall 732. Although the concavity 734 may not be as pronounced as previously-described concavities in the sidewall of a core component, the concavity 734 will help reduce stresses at the junction between the core component 730 and the respective first and second components 710 and 720. Also, note that the concavities 738 and 739 corresponding to convexities 711C and 721C do vary in size and shape from each other. Both groups of concavities 738 and 739 help reduce shear forces in the implant 700 and particularly at the location of the junction between the core components 730 and the first and second components 710 and 720. Consequently, concavities 738 and 739 make it possible to better absorb the shearing forces to which the implant 800 would be subjected. More specifically, the shapes of concavities 738 and 739 make it possible to direct and concentrate the forces of vertical compression toward the center of core component 730. As noted above, however, the greater the amount that the elastomeric material of the core component 730 is allowed to move and thus greater potential for a reduction in shear forces. So, if the core component 730 has concavities 738 and 739 instead of convexities, there is less potential for reduction of shear forces than if convexities were present.

A variety of materials are available to construct any of the components of the implants described herein. For example, the first and second components of any of the implants 100, 200, 300, 400, 500, 600, 700 and 800 may be made of any metal or non-metal biocompatible material. Suitable materials include, but are not limited to, any one or combination of Titanium Alloys, commercially available Titanium, stainless steel, polyetheretherketone ("PEEK"), cobalt chrome ("CoCr"), polyethylene, and ultra high molecular weight polyethylene ("UHMWPE"). Similarly, any inner portion (for example, inner portion 110A) of a first or second component (for example, first component 110 or second component 120) may be composed of different material or materials or may be composed of the same material or materials as its adjoining outer portion (for example, outer portion 110B).

Further, the core components 30, 130, 230, 330, 430, 530, 630 and 730 of any of the implants 100, 200, 300, 400, 500, 600, 700 and 800 may be made of a variety of biocompatible materials. Suitable elastomeric materials for core components include, but are not limited to, any one or combination of polycarbonurethane ("PCU"), polyurethane ("PU"), polyethelene, silicone and hydrogel. Further, any central core component (for example, central core component 435) may be composed of different material or materials or may be composed of the same material or materials as its adjoining outer core component (for example, outer core component 431). Further, two different portions of a core component (for example, core component 430) may be composed of the same material or materials (or a different material or materials), but have different properties. For example, the two portions of core component 430 may be made of the same material, but central core component 435 may be harder or softer than outer core component 431.

As stated above, there is a large variety of shapes and sizes of any of the components of the implants described herein. In one embodiment of spinal implant 100 that would be intended for use in the cervical spine, where the horizontal dimensions (in a direction substantially perpendicular to the central longitudinal axis CLA) of the first component 10 and second component 20 are 17 mm×16 mm, the horizontal dimensions of the core component 30 may be 14 mm×14 mm (thus, distance d1 may be 14 mm), the diameter in the horizontal direction of the central core component (or distance d5) may be 6.4 mm, distance d2 may be 7.6 mm, distances d3 and d4 may be 10.7 mm, the vertical distance (in a direction substantially parallel to the central longitudinal axis CLA) of the concavity 34 at the location of the sidewall 32 may be 0.25 mm, and the vertical distance in which the convexities 38 and 39 extend outward into their respective first and second components 10 and 20 may be 1 mm.

In one embodiment of spinal implant 200 that would be intended for use in the cervical spine, where the horizontal dimensions of the first component 110 and second component 120 are 17 mm×16 mm, the overall height (in the vertical direction) of the implant 110 may be 7.9 mm, the horizontal dimensions of the core component 130 may be 14 mm×14 mm (thus, distance d1 may be 14 mm), distance d5 may be 6.4 mm, distance d2 may be 7.6 mm, distances d3 and d4 may be 10.7 mm, the vertical distance (in a direction substantially parallel to the central longitudinal axis CLA) of the concavity 34 at the location of the sidewall 132 may be 0.25 mm, and the vertical distance in which the convexities 138 and 139 extend outward into their respective first and second components 110 and 120 may be 1 mm.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. For example, a sidewall of a core component need not be substantially vertical (or substantially parallel to the central longitudinal axis) throughout its length between a first inner surface and a second inner surface. That is, a core component sidewall may be curved or angled. As another example, although not shown in any figures, a sidewall of a core component may have multiple concavities. Similarly, although not shown in any figures, a central core component may have multiple concavities or multiple convexities adjacent it corresponding inner surface.

Furthermore, as used herein, the terms components and modules may be interchanged. It is understood that all spatial references, such as "first," "second," "exterior," "interior," "superior," "inferior," "anterior," "posterior," "central," "annular," "outer," and "inner," and are for illustrative purposes only and can be varied within the scope of the disclosure.

The invention claimed is:

1. A spinal implant comprising:
a first component comprising:
a first exterior surface configured for engaging a first vertebra; and
a first interior surface opposing the first exterior surface;
a second component comprising:
a second exterior surface configured for engaging a second vertebra; and
a second interior surface opposing the second exterior surface; and a
a core component situated between the first and second components and adhered thereto such that a first exterior surface of the core component engages and is fixed to the first interior surface and a second exterior surface of the core component engages and is fixed to the second interior surface, wherein at least one of the first interior surface and the second interior surface comprises a concavity such that at a location of the concavity, the core component comprises a corresponding convexity, wherein the core component has a diameter that is smaller than a diameter of the first component and a diameter of the second component and further comprises a sidewall, the sidewall includes a concavity extending into the sidewall a uniform distance 360 degrees around a central longitudinal axis of the spinal implant in a single plane.

2. The spinal implant of claim 1, wherein each of the first interior surface and the second interior surface comprise a concavity such that, at the location of the concavities, the core component comprises corresponding convexities.

3. The spinal implant of claim 1, wherein the first component and the second component are rigid and the core component includes an elastomeric material.

4. The spinal implant of claim 1, wherein the first component and the second component each comprise a metal material.

5. The spinal implant of claim 1, wherein the core component is monolithic and consists of an elastomeric material.

6. The spinal implant of claim 1, wherein spinal implant further comprises:
the central longitudinal axis situated substantially in a center of the spinal implant, wherein along the central longitudinal axis, the components of the spinal implant are situated in an order of first component, core component and second component, wherein:
the core component extends over a first distance in a direction substantially perpendicular to the central longitudinal axis; and
the concavity in the sidewall of the core component extends over a second distance in a direction substantially perpendicular to the central longitudinal axis, wherein the second distance is more than half of the first distance.

7. The spinal implant of claim 6, wherein the concavity in the sidewall of the core component is situated at a location about the central longitudinal axis that is substantially midway between the first interior surface and the second interior surface and substantially perpendicular to the central longitudinal axis.

8. The spinal implant of claim 6, wherein:
the concavity in the first interior surface and the concavity in the second interior surface each lie about the central longitudinal axis and each concavity lies in a direction substantially parallel to the central longitudinal axis and spans an area that extends substantially perpendicular to the central longitudinal axis along the first interior surface and the second interior surface, respectively; and
the concavity in the first interior surface extends over a third distance about the central longitudinal axis and the concavity in the second interior surface extends over a fourth distance about the central longitudinal axis; and
at the location of the concavity in the sidewall of the core, the core component extends in a direction substantially perpendicular to the central longitudinal axis for a fifth distance, wherein each of the third and fourth distances are greater than the fifth distance.

9. The spinal implant of claim 6, wherein the concavity in the sidewall of the core component defines a central core portion of the core component and portions of the core component above and below the central core portion are softer than the central core portion.

10. The spinal implant of claim 1, wherein at least a portion of the concavity in the sidewall is substantially transverse to the central longitudinal axis.

11. The spinal implant of claim 1, wherein:
the first interior surface includes opposite first and second planar portions; and
the first interior surface includes concave portion positioned between the first and second planar portions, the concave portion having a continuous radius of curvature.

12. The spinal implant of claim 1, wherein:
the first interior surface includes opposite first and second planar portions; and
the first interior surface includes a concave portion positioned between the first and second planar portions, the concave portion being continuously curved between an interface between the first planar portion and the concave portion and an interface between the second planar portion and the concave portion.

13. The spinal implant of claim 1, wherein:
the first component extends between opposite first and second end surfaces, the first and second end surfaces extending between opposite first and second side surfaces; and
the first exterior surface is convexly curved between the first and second end surfaces and between the first and second side surfaces.

14. The spinal implant of claim 1, wherein the core component comprises an elastomeric material, wherein the elastomeric material is polycarbonurethane, polyurethane, polyethelene, silicone or hydrogel.

15. The spinal implant of claim 1, wherein:
the core component has a maximum diameter extending a first distance along a transverse axis that extends perpendicular to the central longitudinal axis; and
the concavity of the core component extends a second distance along the transverse axis, the second distance being more than half of the first distance.

16. A spinal implant comprising:
a first component comprising:
a first exterior surface configured for engaging a first vertebra; and
a first interior surface opposing the first exterior surface;
a second component comprising:
a second exterior surface configured for engaging a second vertebra; and
a second interior surface opposing the second exterior surface; and
a monolithic core component situated between the first and second components and adhered thereto such that a first exterior surface of the core component engages and is fixed to the first interior surface and a second exterior surface of the core component engages and is fixed to the second interior surface, wherein at least one of the first interior surface and the second interior surface comprises a concavity such that at a location of the concavity, the core component comprises a corresponding convexity, and wherein the core further comprises a sidewall, wherein the sidewall comprises a concavity, wherein the core component has a diameter that is smaller than a diameter of the first component and a diameter of the second component and further comprises a sidewall, the sidewall includes a concavity extending into the sidewall a uniform distance 360 degrees around a central longitudinal axis of the spinal implant in a single plane, the concavity in the sidewall forms a solid central core component.

17. The spinal implant of claim 16, wherein the first component and the second component each comprise a metal material and the core component consists of an elastomeric material.

18. The spinal implant of claim 16, wherein the spinal implant further comprises:
the central longitudinal axis situated substantially in a center of the spinal implant, wherein along the central longitudinal axis, the components of the spinal implant are situated in an order of first component, core component and second component, wherein:
the core component extends over a first distance in a direction substantially perpendicular to the central longitudinal axis; and
the concavity in the sidewall of the core component extends over a second distance in a direction substantially perpendicular to the central longitudinal axis, wherein the second distance is more than half of the first distance.

19. The spinal implant of claim 18, wherein:
the concavity in the first interior surface and the concavity in the second interior surface each lie about the central longitudinal axis and each concavity lies in a direction substantially parallel to the central longitudinal axis and spans an area that extends substantially perpendicular to the central longitudinal axis along the first interior surface and the second interior surface, respectively; and
the concavity in the first interior surface extends over a third distance about the central longitudinal axis and the concavity in the second interior surface extends over a fourth distance about the central longitudinal axis; and
at the location of the concavity in the sidewall of the core, the core component extends in a direction substantially perpendicular to the central longitudinal axis for a fifth distance, wherein each of the third and fourth distances are greater than the fifth distance.

20. A spinal implant comprising:
a first component comprising:
a first exterior surface configured for engaging a first vertebra; and
a first interior surface opposing the first exterior surface;
a second component comprising:
a second exterior surface configured for engaging a second vertebra; and
a second interior surface opposing the second exterior surface; and
a core component situated between the first and second components and adhered thereto such that a first exterior surface of the core component engages and is at least provisionally fixed to the first interior surface and a second exterior surface of the core component engages and is at least provisionally fixed to the second interior surface, wherein at least one of the first interior surface and the second interior surface comprises a concavity such that at a location of the concavity, the core component comprises a corresponding convexity, wherein the core component further comprises a sidewall including a concavity extending into the sidewall 360 degrees around a central longitudinal axis of the spinal implant in a single plane.

* * * * *